United States Patent [19]

Hauke et al.

[11] Patent Number: 4,737,284
[45] Date of Patent: Apr. 12, 1988

[54] CHROMATOGRAPHY COLUMN

[75] Inventors: Günter Hauke, Mühltal; Günter Sättler, Reinheim, both of Fed. Rep. of Germany

[73] Assignee: Merck Patent Gesellschaft mit beschranker Haftung, Darmstadt, Fed. Rep. of Germany

[21] Appl. No.: 869,549

[22] Filed: Jun. 2, 1986

[30] Foreign Application Priority Data

Jun. 1, 1985 [DE] Fed. Rep. of Germany ....... 3519725

[51] Int. Cl.[4] ............................................. B01D 15/08
[52] U.S. Cl. ................................... 210/198.2; 55/386; 285/393
[58] Field of Search ................ 210/198.2; 55/386; 285/356, 387, 388, 393

[56] References Cited

U.S. PATENT DOCUMENTS

| Re. 31,974 | 8/1985 | Brownlee | 55/386 |
|---|---|---|---|
| 944,877 | 12/1909 | Koschinski | 285/388 |
| 3,298,160 | 1/1967 | Hoffman | 55/386 |
| 3,488,073 | 1/1970 | Wold | 285/388 |
| 3,679,237 | 7/1972 | DeAngelis | 210/198.2 |
| 3,763,879 | 10/1973 | Jaworek | 210/198.2 |
| 3,855,130 | 12/1974 | Randau | 55/386 |
| 4,050,722 | 9/1977 | Berger | 285/388 |
| 4,070,284 | 1/1978 | Fujita | 210/198.2 |
| 4,343,496 | 8/1982 | Petranto | 285/387 |
| 4,524,998 | 6/1985 | Brisco | 285/388 |
| 4,551,249 | 11/1985 | Shackelford | 210/198.2 |
| 4,565,632 | 1/1986 | Hatch | 55/386 |

FOREIGN PATENT DOCUMENTS

| 2930962 | 2/1981 | Fed. Rep. of Germany ... 210/198.2 |
|---|---|---|
| 3021306 | 12/1981 | Fed. Rep. of Germany ... 210/198.2 |
| 3143075 | 5/1983 | Fed. Rep. of Germany ... 210/198.2 |

*Primary Examiner*—Ernest G. Therkorn
*Attorney, Agent, or Firm*—Millen & White

[57] ABSTRACT

The invention relates to a chromatography columns, consisting of metal tubes which are filled with sorbent and which are provided at both ends with distributed and sealing elements. Screw unions for connecting capillaries are utilized, which unions consist at least of a supporting nut fitted to the column tube and a cap nut. The supporting nuts consist of two half-shells which can be removed from the column tube after the cap nut has been unscrewed. By so configuring the columns, the same tube column can optionally accommodate precolumns.

1 Claim, 2 Drawing Sheets

CHROMATOGRAPHY COLUMN

BACKGROUND OF THE INVENTION

1. Field of the Invention

This invention relates to chromatography columns consisting of metal tubes which are filled with sorbent; which are provided at both ends with distribution and sealing elements, and which optionally may include a precolumn.

2. Technical Considerations and Prior Art

Numerous columns for chromatography are known. Usually these columns have an external thread or a supporting nut with an internal or external thread at both ends. Capillary connections with these threads for the supply and discharge of eluant can be made by utilizing a threaded stopper or a cap nut.

Recently, column cartridges have been offered which do not have screw unions, but rather are clamped either into a cartridge holder, as described for example, in German Offenlegungsschrift No. 2,930,962; German Offenlegungsschrift No. 3,021,306, and U.S. Pat. No. 4,283,280, or inserted into a column-clamping device as is disclosed in German Offenlegungsschrift No. 3,143,075.

For a supplier who desires to supply his customers both precolumn cartridges and columns with only a reducing screw union, considerable costs are incured due to the necessity for two-track manufacturing and double stocking. Accordingly, there is a need for chromatography columns which can be used both with cartridge precolumns and without cartridge precolumns.

SUMMARY OF THE INVENTION

The instant invention relates to a chromatography column, consisting of a metal tube which is filled with a sorbent and which is provided at both ends with a distribution element and a sealing element. A screw union for connecting capillaries is provided, which union consists at least of a supporting nut fitted to the column tube and a cap nut. The improvement is characterized mainly in that the supporting nut consists of two half-shells which can be removed from the column tube after the cap nut has been unscrewed.

The configuration according to the invention has the advantage that in the future only one model of each column-type need be supplied and the further advantage of reducing the expense of screw unions. This is due substantially to the fact that only one pair of screw unions is required for chromatography columns of a given diameter. Accordingly, when changing columns, only the cartridge and cap nut need be changed, whereas the same screw union can still be used. For the user, this means considerable savings in purchase cost.

BRIEF DESCRIPTION OF THE DRAWINGS

Various other objects, features and attendant advantages of the present invention will be more fully appreciated as the same becomes better understood when considered in connection with the accompanying drawings, in which like reference characters designate the same or similar parts throughout the several views.

The drawings show a preferred embodiment of columns according to the instant invention. Since the columns are preferably of symmetrical structure, only one end of a column has been illustrated in each case.

DESCRIPTION OF THE PREFERRED EMBODIMENT

Figure 1:
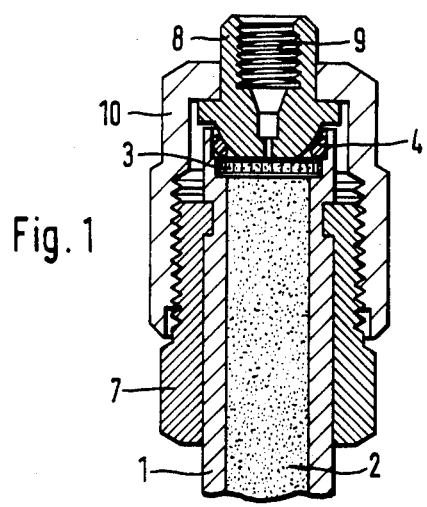
FIG. 1 shows a section through a column end with a screw union fitted.

The column tube (1) is usually charged with a sorbent (2) and sealed with a distribution element (3) and a gasket (4) for delivery to the customer. The column tube (1) can be used in this form, for example, in a cartridge holder or in a column-clamping device. In the vicinity of the column end, an annular groove (5) is provided in which a rib (6) of the supporting nut (7), which divided into two parts, can engage. A thrust member (8) is provided with a threaded bore (9) and is pressed against the gasket (4) by means of the cap nut (10) which is screwed down against the supporting nut (7) so as to make a seal.

Figure 2:
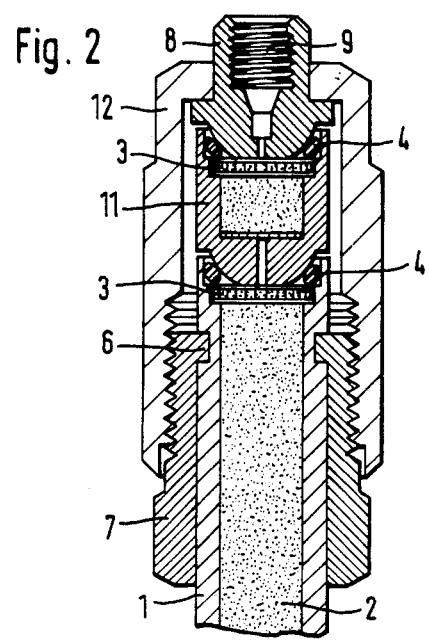
FIG. 2 shows a section through a column end with a precolumn inserted into a screw union.
Figure 3:
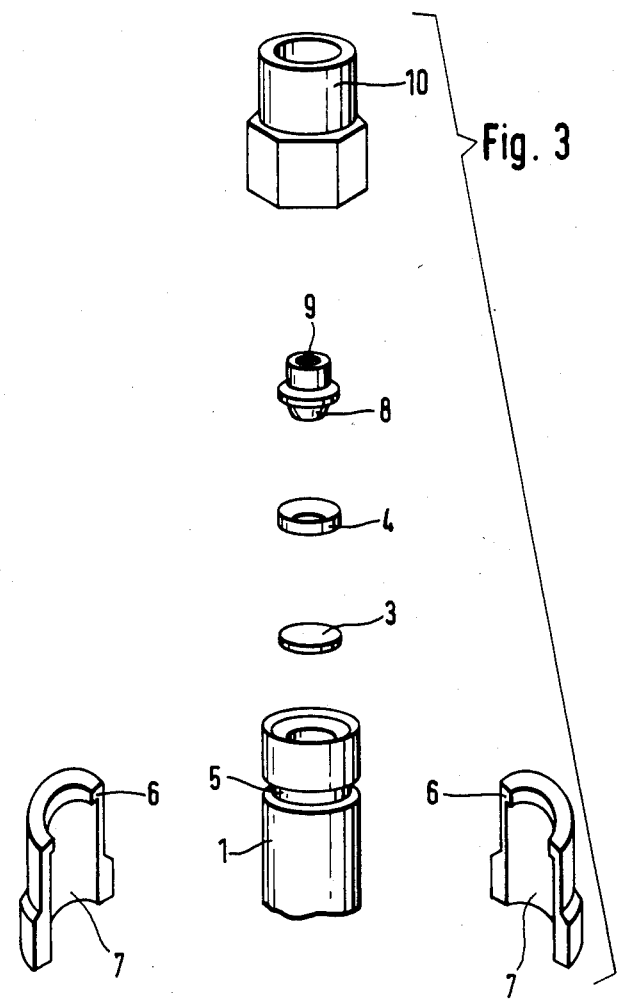
FIG. 3 shows a column end with a screw union in an exploded view.

By simply screwing on a few components, a cartridge-type column (FIG. 2) can be transformed into a column without a cartridge (FIG. 1).

It is likewise very easy to configure the column (1) according to the invention with a precolumn (11). For this purpose, the cap nut (10) is replaced by a longer nut (12). For sealing the column, for example during transport, the thrust member (8) can be closed by a blank plug (not shown).

The columns (1) according to the invention can be provided in any desired lengths and diameters and, as already mentioned, only one pair of screw unions need be purchased in each case for columns of identical diameter. Conventional materials such as, in particular, stainless steel are used for the column and the screw union. The gasket (4) is preferably made of inert polymers such as, for example, PTFE whereas the distribution element (3) can consist of sintered metal, ceramics or fabric.

By utilizing the aforementioned structure, a chromatography column supply system is provided wherein there are a plurality of chromatography columns (1) and a lesser number of chromatography precolumns (11) configured for use with at least some of the chromatography columns. Each of the chromatography columns (1) have first and second ends which are identical in that the external grooves (5) and the internal shoulders which support the distribution elements (3) and seals (4) are the same. The support nuts (7) for the ends of each column are identical in that each support nut is of the same length and is comprised of two mirror-image half-shells having internally projecting, semi-circular ribs which are received in one-half of the groove (5) in the precolumn (1). The same distribution element (3) is utilized by each precolumn (1) as is the same thrust member (8).

The only difference in the components of the supply system is that the cap nuts (12) are longer than the cap nuts (10), since the cap nuts (12) are used with the precolumn (11). In this way, one need only stock a single type of chromatography column (1), support nut (7), and thrust member (8). The only variation in stocked items are the cap nuts (10) and (12) which are interchangeable with the standard columns (1) of the same diameter.

Owing to the easy handling, inexpensive purchase and stockholding, an advantageous new chromatography column (1) is available for chromatography.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A chromatography column supply system wherein there are a plurality of chromatography columns containing sorbent and a lesser number of chromatography precolumns configured for use with some of the chromatogaphy columns, the improvement comprising:

each chromatography column having first and second ends which are identical, the ends each column including an external groove and having internal, outwaradly facing shoulders;

identical support nuts for each end, each support nut comprising two mirror image half-shells each having an internally projecting semicircular rib which is received in one half of the groove;

a distribution element positioning in each column in abuttment with one of the shoulders and in engagement with the sorbent in the column;

a thrust member for each column; the thrust member engaging the distribution element if the column does not use a precolumn, and engaging the precolumn if the column uses a precolumn;

first cap nuts having selected lengths, internal threads for threadably engaging with the support nuts, and shoulders for engaging the thrust members to urge the thrust members into abutment with distribution element, and second cap nuts each having a length greater than the length of the first cap nuts, internal threads for threadably engaging the external threads of the support nuts and shoulders for engaging thrust members to urge the thrust members into abutment with precolumns; whereby more than one type of chromatography column need not be stocked for use either with or without precolumns.

* * * * *